(12) United States Patent
Kurz (10) Patent No.: US 7,125,669 B2
(45) Date of Patent: Oct. 24, 2006

(54) SOLID-PHASE IMMOBILIZATION OF PROTEINS AND PEPTIDES

(75) Inventor: Markus Kurz, Newton, MA (US)

(73) Assignee: Compound Therapeutics, Inc., Waltham, MA (US)

(*) Notice: Subject to any disclaimer, the term of this patent is extended or adjusted under 35 U.S.C. 154(b) by 497 days.

(21) Appl. No.: 10/302,456

(22) Filed: Nov. 21, 2002

(65) Prior Publication Data

US 2003/0100004 A1 May 29, 2003

Related U.S. Application Data

(60) Provisional application No. 60/333,470, filed on Nov. 27, 2001.

(51) Int. Cl.
*C12Q 1/68* (2006.01)
*G01N 33/53* (2006.01)
*C07H 21/02* (2006.01)
*C07H 21/04* (2006.01)

(52) U.S. Cl. .................. 435/6; 435/7.1; 536/23.1; 536/24.3

(58) Field of Classification Search .............. 435/6, 435/7.1; 536/23.1, 24.3
See application file for complete search history.

(56) References Cited

U.S. PATENT DOCUMENTS

| | | | |
|---|---|---|---|
| 5,843,701 A | | 12/1998 | Gold et al. |
| 6,207,446 B1 * | | 3/2001 | Szostak et al. .......... 435/287.2 |
| 6,258,558 B1 * | | 7/2001 | Szostak et al. ............ 435/69.1 |
| 6,261,804 B1 | | 7/2001 | Szostak et al. |
| 6,281,344 B1 * | | 8/2001 | Szostak et al. ............ 536/23.1 |
| 6,406,921 B1 | | 6/2002 | Wagner et al. |
| 6,429,300 B1 * | | 8/2002 | Kurz et al. ................. 536/23.1 |
| 6,436,665 B1 * | | 8/2002 | Kuimelis ................... 435/68.1 |
| 6,489,116 B1 * | | 12/2002 | Wagner ......................... 435/6 |
| 6,518,040 B1 * | | 2/2003 | Ehrenberg et al. ......... 435/69.1 |
| 6,537,749 B1 * | | 3/2003 | Kuimelis et al. .............. 435/6 |
| 6,602,685 B1 * | | 8/2003 | Lohse ....................... 435/69.1 |

FOREIGN PATENT DOCUMENTS

| WO | WO 98/31700 | 7/1998 |
|---|---|---|
| WO | WO 00/32823 A1 | 6/2000 |
| WO | WO 00/47775 | 8/2000 |
| WO | WO 01/07657 A1 | 2/2001 |

OTHER PUBLICATIONS

Roberts et al., RNA-peptide fusions for the in vitro selection of peptides and proteins. PNAS 94 : 12297-12302 (Nov. 1997).*
Ellman, J., et al., "Biosynthetic Method for Introducing Unnatural Amino Acids Site-Specifically into Proteins," Methods in Enzymology, 202:301-336 (1991).
Fraser, T.H. and Rich, A., "The Preparation of tRNA Terminating in 3'-Amino-3'-deoxyadenosine and 2'-Amino-2'-deoxyadenosine," Methods in Enzymology, 59:134-145 (1979).
Kurz, M., et al., "Psoralen photo-crosslinked mRNA-puromycin conjugates: a novel template for the rapid and facile preparation of mRNA-protein fusions," Nucleic Acids Research, 28(18):1-5 (2000).
Liu et al., "Optimized synthesis of RNA-protein fusions for in vitro protein selection", Methods in Enzymology, 318: 268-293 (2000).
Matzke, A.J.M., et al., "Mechanism of translocation: Relative arrangement of tRNA and mRNA on the ribosome," Proc. Natl. Acad. Sci. USA, 77(9):5110-5114 (1980).
Roberts, R.W. and Szostak, J.W., "RNA-peptide fusions for the *in vitro* selection of peptides and proteins," Proc. Natl. Acad. Sci. USA, 94:12297-12302 (1997).
Roberts, R.W., "Totally *in vitro protein* selection using mRNA-protein fusions and ribosome display," Current Opinion in Chemical Biology, 3: 268-273 (1999).

* cited by examiner

*Primary Examiner*—Ethan Whisenant
*Assistant Examiner*—L. Humes
(74) *Attorney, Agent, or Firm*—Fish & Neave IP Group of Ropes & Gray LLP (57) ABSTRACT

Disclosed herein are methods for immobilizing a peptide or protein on a solid support. The method generally includes the following steps: (a) providing one or more templates attached to a solid support, wherein the one or more templates include (i) an RNA encoding a peptide and (ii) a peptide acceptor-linker linked to the RNA; and (b) subjecting the one or more templates to conditions that support translation and attachment of said peptide to said peptide acceptor, thereby synthesizing the one or more peptides on the solid support. Also disclosed herein are solid supports having at least one RNA-protein fusion component immobilized thereon, methods for generating protein arrays, and methods for screening molecules using these arrays.

8 Claims, 5 Drawing Sheets

Figure 1

Solid-Phase Attachment of Biotin-modified Puromycin Linker

Figure 2

Solid-Phase Attachment of Puromycin Linker

Synthesis of Protein Arrays

Figure 5

SEQUENCE LISTING

```
<160> NUMBER OF SEQ ID NOS: 2

<210> SEQ ID NO 1
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 1

Met Val Ser Asp Val Pro Arg Asp Leu Glu Val Val Ala Ala Thr Pro
1               5                   10                  15

Thr Ser Leu Leu Ile Ser Trp Lys Thr His Glu Val Ala Ala Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Trp Ala Ser Ile Ala Thr Ile Ser Gly Leu Lys
    50                  55                  60

Pro Gly Val Asp Tyr Thr Ile Thr Val Tyr Ala Val Thr Pro Leu Arg
65                  70                  75                  80

Trp Thr Glu Thr Glu Ala His Ile Pro Ile Pro Ile Asn Tyr Arg Thr
                85                  90                  95

<210> SEQ ID NO 2
<211> LENGTH: 12
<212> TYPE: RNA
<213> ORGANISM: Artificial Sequence
<220> FEATURE:
<223> OTHER INFORMATION: Linker

<400> SEQUENCE: 2
uagcggaugc cc                                                   12
```

SOLID-PHASE IMMOBILIZATION OF PROTEINS AND PEPTIDES

CROSS REFERENCE TO RELATED APPLICATIONS

This application claims the benefit of the filing date of U.S. provisional application, U.S. Ser. No. 60/333,470, filed Nov. 27, 2001, hereby incorporated by reference.

BACKGROUND OF THE INVENTION

In general, the present invention relates to methods for immobilizing peptides and proteins onto a solid support.

Proteins are known to interact specifically with other molecules, such as other proteins, nucleic acids, and small-molecules, based on the three-dimensional shapes and electronic distributions of those molecules. Through these interactions, proteins are responsible for regulating a wide variety of biological processes. The discovery of compounds that interact with proteins can lead to the identification of new drug targets and the development of pharmaceutical products.

One way to search for new drug candidates is to screen large libraries of natural materials or synthesized molecules, using assay techniques that range in complexity from simple binding reactions to elaborate physiological preparations. Unfortunately, the isolation of compounds that bind specifically to biologically important molecules is difficult, in part because the selection of molecules of interest from large ensembles or repertoires is time-consuming, laborious, and costly. As advances in technology allow for the generation of larger libraries of compounds, there is a need for high throughput systems that allow for rapid and efficient screening of large numbers of compounds.

One method for screening involves the preparation of chips that include arrays of candidate molecules immobilized on a solid support. The first such arrays were nucleic acids. Proteins, however, are more difficult to immobilize and screen. It is important for proteins to have the proper orientation to ensure accessibility of their active sites to interacting molecules. Consequently, maintaining the activity of immobilized proteins at the liquid-solid interface requires different immobilization strategies than for nucleic acids.

Currently, methods for the immobilization of proteins on a support for application as screening devices involve immobilization of free proteins in solution. However, these methods are not possible with all proteins, such as when the protein is insoluble or difficult to purify. Another problem arises because covalent protein immobilization is usually carried out non-specifically by reaction of functional groups of amino acid residues throughout the protein with appropriately derivatized surfaces. This approach renders some proteins inactive due to disruption of protein structure and/or inaccessibility of the protein's binding or active sites. Even if such sites are exposed, the immobilized protein may be too close to the solid support surface to allow for interaction with reagents in the solution phase. Moreover, even though some of the immobilized proteins do retain functionality, a certain fraction of the protein sample will generally be inactive, resulting in a heterogeneous population.

Improved methods for immobilizing proteins onto a solid support are needed so that proteins exhibiting limited solubility, proteins that are difficult to purify, or proteins that are sensitive to inactivation by current immobilization techniques can be immobilized.

SUMMARY OF THE INVENTION

The present invention features a solid support having at least one RNA-protein fusion component immobilized thereon, wherein the RNA-protein fusion component includes a protein covalently bonded at its C-terminus to a peptide acceptor, wherein the peptide acceptor is joined through a linker to the RNA encoding the protein, the RNA-protein fusion component being attached to the solid support by the interaction of the linker and the solid support. In a preferred embodiment, the linker includes a biotin component and the solid support includes a steptavidin component. Attachment of the linker to the solid support results from the binding of the biotin component to the streptavidin component. In other preferred embodiments, the linker includes a sequence, for example a PNA sequence, that is complementary to a portion of the RNA and is hybridized to the portion of the RNA. In another embodiment, the linker further includes a psoralen moiety that is cross-linked to the RNA. The solid support may include a plurality of immobilized proteins that form an array.

In a related aspect, the invention features a method of creating an array of immobilized proteins. The method involves the steps of: (a) providing a solid support on which an array of templates are immobilized, wherein the templates include (i) an RNA encoding a peptide and (ii) a peptide acceptor-linker linked to the RNA; and (b) subjecting the array of templates to conditions that support translation and attachment of the peptide to the peptide acceptor, thereby generating an array of peptides. In this array each peptide is individually bound a peptide acceptor, and the peptides are thereby immobilized onto the solid support. The templates can be attached to the solid support either through the RNA portion of the template or through the peptide acceptor-linker portion of the template. In preferred embodiments, the solid support is a microchip or beads, wherein all of the peptides that are immobilized on an individual bead are the same.

Solid supports or arrays according to the invention can be used to screen large collections of compounds to identify potential drug targets. Accordingly, in another aspect, the invention provides a method for screening a population of molecules for their ability to interact with a protein. The method involves contacting the population of molecules with a solid support or an array according to the invention, followed by detecting an interaction of a molecule in the population with an immobilized protein of the solid support or array. The detection can be either direct, for example detecting labeled components of the sample, or indirect, for example using a secondary antibody.

In yet another related aspect, the invention features a method for screening a plurality of proteins for their ability to interact with a component of a sample, the method involving the steps of: providing a solid support according to the invention; contacting the sample with the solid support; and detecting an interaction of a component of the sample with an immobilized protein of the solid support.

In another aspect, the invention features a method for synthesizing one or more peptides on a solid support. The method involves providing one or more templates attached to a solid support, the one or more templates including (i) an RNA encoding a peptide and (ii) a peptide acceptor-linker linked to the RNA. The one or more templates are subjected to conditions that support translation and attachment of the peptide to the peptide acceptor, thereby synthesizing the one or more peptides on the solid support.

In preferred embodiments of the invention, the peptide acceptor is puromycin and the puromycin may be linked to the 3' end of the RNA; the peptide acceptor-linker is linked at the 3' end of the RNA; and the solid support is a chip, bead, membrane, or plastic surface.

Any suitable derivatization or solid phase binding method may be used to attach the one or more templates to the support. For instance, the one or more templates may be functionalized with an amino group and attachment may be accomplished using amino capture techniques. Alternatively, the one or more templates may be modified to include the first member of a capture pair (e.g., biotin). The one or more templates are then immobilized by exposure to a solid support that includes the second member of the capture pair (e.g., streptavidin). In yet another alternative, a first member of a capture pair is immobilized on the solid support, a second member of the capture pair is linked to the one or more templates, and the attaching is accomplished by interaction of the first and second members. Examples of capture pairs include, but are not limited to, antibody-antigen (or hapten) pairs, ligand-receptor pairs, biotin-avidin pairs, polynucleotides with complementary base pairs, enzyme-substrate pairs, lectin-carbohydrate pairs, and the like. A preferred capture pair is biotin-streptavidin.

In one embodiment of the invention, the one or more templates are attached to the solid support through the nucleic acid portions (for example, the RNA portions) of the one or more templates. The nucleic acid (for example, RNA) can be attached to the support either before or after being linked to the peptide acceptor which has a linker attached.

In an alternative embodiment, the one or more templates are attached to the solid support through the peptide acceptor-linker portion. There are a variety of ways of attaching the peptide acceptor-linker to the solid support. For example, the peptide acceptor-linker may be modified to contain functional groups (e.g., amine, thiol) that facilitate attachment of the peptide acceptor-linker to the support. In a preferred embodiment, the peptide acceptor-linker includes a side chain through which the template is attached to the support. Suitable side chains include, without limitation, long alkyl- or polyethylene glycol chains.

In a preferred embodiment, the one or more templates are attached to the solid support by first attaching the peptide acceptor-linker to the solid support followed by attaching (for example, cross-linking) the nucleic acid (for example, RNA) to the peptide acceptor-linker. Alternatively, the nucleic acid may be cross-linked to the peptide acceptor prior to immobilization of the template.

One advantage of attaching the template to the solid support through the linker portion is that, following the translation reaction, it is possible to remove the RNA portion of the template from the solid support while leaving the linker portion of the template intact without detaching the protein. The RNA, which can be rather large, is removed from the solid support by any method suitable for removing RNA, for example, by nuclease or hydroxide treatment.

In another preferred embodiment, an array of templates is attached to the solid support, thereby generating an array of immobilized peptides. Preferably, the solid support is a chip or a plurality of beads wherein all of the peptides immobilized on an individual bead are the same.

By providing a means for synthesizing a protein directly on the surface of a solid support, the invention provides means for immobilizing proteins with low solubility, proteins which are not easily purified, and large proteins, which otherwise may be difficult to immobilize. The RNA templates used in the present invention can be immobilized by known chemistries with use of commercially available reagents making them easier to work with than protein compounds.

The methods described herein allow for C-terminal immobilization of a protein, which results in a controlled and uniform orientation and representation of the protein. In addition, the invention presents fewer restrictions regarding the size and nature of proteins that can be immobilized, since any peptide that can be expressed in vitro by the RNA-protein fusion method is amenable to attachment using this methodology. The invention also eliminates the loss of protein that ordinarily results from inefficient immobilization chemistry.

Other advantages and features of the invention will be apparent from the following detailed description and from the claims.

DEFINITIONS

The terms "protein," "polypeptide," and "peptide" are used interchangeably herein and refer to any chain of two or more naturally occurring or modified amino acids joined by one or more peptide bonds, regardless of post-translational modification (e.g., glycosylation or phosphorylation).

By "solid support" is meant any rigid or semi-rigid material to which a molecule, such as a protein or nucleic acid, binds or can be attached. The support can be any porous or non-porous water insoluble material, including without limitation, membranes, filters, chips, slides, wafers, fibers, magnetic or nonmagnetic beads, gels, tubing, strips, plates, rods, polymers, particles, microparticles, capillaries, and the like. The support can have a variety of surface forms, such as wells, trenches, pins, channels and pores.

By a "peptide acceptor" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202:301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure.

By a peptide acceptor being positioned "at the 3' end" of a nucleic acid is meant that the peptide acceptor molecule is positioned after the final codon of the protein coding sequence of the nucleic acid. This term includes, without limitation, a peptide acceptor-linker that is positioned precisely at the 3' end of the protein coding sequence as well as one which is separated from the final codon by intervening coding or non-coding sequences (for example, a sequence corresponding to a pause site). This term also includes constructs in which coding or non-coding sequences follow (that is, are 3' to) the peptide acceptor molecule. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence or PNA sequence that binds at or near the 3' end of the protein coding sequence and that itself is bound to a peptide acceptor molecule.

By "template" is meant a nucleic acid molecule that includes a peptide-encoding RNA that is linked to a peptide acceptor-linker. The template is used for the preparation of RNA-protein fusions that include a peptide or protein sequence covalently linked via its C-terminus to the 3' end of its own RNA. The "template" includes a start codon and translation initiation signals.

By "attached" is meant that one molecule is bound (covalently or non-covalently) to a solid support or to another molecule.

By a "linker" or "linker molecule" is meant a sequence that includes oligonucleotides, including deoxyribonucleotides or analogs thereof. In a preferred embodiment, the linker carries a 5'-terminal psoralen moiety. Alternatively, the linker can include polyethylene glycol (PEG), or other appropriate non-nucleotide compounds for flexibility.

By "RNA" is meant a sequence of two or more covalently bonded, naturally occurring or modified ribonucleotides. One example of a modified RNA included within this term is phosphorothioate RNA.

By an "array" is meant a fixed pattern of at least two different immobilized objects e.g., proteins) on a solid support. Preferably, the array includes at least $10^2$, more preferably, at least $10^3$, and, most preferably, at least $10^4$ different members. For array production, a plurality of nucleic acid-peptide acceptor templates are immobilized on a solid support, and a translation reaction is performed to generate an array of immobilized proteins. Arrays of proteins produced by the technique described herein are particularly useful for large scale screening for molecular interactions with other compounds.

By a "population" is meant more than one molecule. A "population" according to the invention preferably means more than $10^1$ molecules, more preferably, more than $10^2$ molecules, and, most preferably, more than $10^3$ molecules.

BRIEF DESCRIPTION OF THE DRAWINGS

FIGS. 4A and 4B are schematic diagrams together showing protein-RNA fusion formation on a solid support. In FIG. 4A, an mRNA is attached to the support through a psoralen-puromycin-linker. In FIG. 4B, in vitro translation generates an mRNA-protein fusion attached to the support via the psoralen-puromycin-linker. After formation of the fusion, the mRNA-puromycin-linker portion of the fusion is removed.

DETAILED DESCRIPTION

The present invention provides a method for solid-phase immobilization of proteins through the formation of RNA-protein fusions. The method involves immobilizing a template onto a solid support. The template includes a peptide acceptor that is linked to an RNA encoding a protein. The immobilized template is used to synthesize the protein directly on the solid support through an in vitro translation reaction, which results in the formation of a RNA-protein fusion attached to the support.

A preferred template for use in the present invention includes an mRNA molecule with a peptide acceptor covalently linked to its 3' end, as is described, for example, in U.S. Pat. Nos. 6,258,558 B 1; 6,261,804 B1; WO 98/31700; WO 00/47775; Roberts & Szostak, Proc. Natl. Acad. Sci. USA 1997, 94:12297; Liu et al., Methods Enzymol. 2000, 318:268; Roberts, Curr. Opin. Chem. Biol. 1999, 268; and Kurz et al., Nucleic Acids Res., 2000, 28:e83. Translation of the mRNA generates a nascent protein. Under appropriate conditions, the C-terminus of the nascent protein covalently links to the peptide acceptor, resulting in a protein that is bound to its own mRNA. Since, in the present invention, the template is attached to a solid support, the linkage of the nascent protein to the peptide acceptor results in immobilization of the protein.

In one embodiment of the invention, puromycin is the peptide acceptor. Puromycin is known to be a nucleoside analog that adds to the C-terminus of a growing peptide chain and terminates translation. In the preferred template, the puromycin (or other peptide acceptor) is bound to a linker. The linker is generally an oligonucleotide, preferably between 25 and 40 nucleotide units in length. The linker region of the peptide could also include non-nucleotide moieties, for example, polyethylene glycol.

Besides puromycin, other suitable peptide acceptors include t-RNA-like structures and other compounds that accept a nascent peptide chain. Such compounds include, but are not limited to, compounds characterized by an amino acid linked to an adenine or an adenine-like compound, such as the amino acid nucleotides, phenylalanyl-adenosine (A-Phe), tyrosyl adenosine (A-Tye), and alanyl adenosine (A-Ala), as well as amide linked structures, such as phenylalanyl 3' deoxy 3' amino adenosine, alanyl 3' deoxy 3' amino adenosine, and tyrosyl 3' deoxy 3' amino adenosine; in any of these compounds, any of the naturally-occurring L-amino acids or their analogs may be utilized. Also included as peptide acceptors are yeast tRNA$^{phe}$ containing the Wye base (Matzke et al., PNAS 77:5110–14, 1980), modified to form a stable amide linkage 3'-deoxy-3'-amino adenosine (Fraser et al., Meth. Enzymol. 59:134–45, 1979). See U.S. Pat. No. 5,843,701.

The RNA molecule of the template may be generated by any standard approach, including normal cellular synthesis, recombinant techniques, and chemical synthesis. Peptide acceptor molecules may also be prepared by any standard technique, for example, techniques described in Roberts and Szostak (Proc. Natl. Acad. Sci. USA, 1997, 94:12297), Szostak et al. (WO 98/31700), Szostak et al., U.S. Pat. No. 6,261,804 B1 (WO 00/47775); and Kurz et al., (Nucleic Acids Res., 2000, 28:e83).

Formation and Immobilization of Template

Methods for covalently linking a peptide acceptor to a nucleic acid molecule are presented in Szostak et al., U.S. Pat. No. 6,261,804 B1; WO 00/47775; and Kurz et al., U.S. Pat. No.6,429,300 B1; WO 01/07657. Enzymatic techniques may be used to join the nucleic acid and the peptide acceptor linker, using, for example, ligase or any other enzyme that is capable of joining two nucleotide sequences. In a preferred approach, the peptide acceptor is attached to an RNA molecule using photochemical methods, as described, for example, in Kurz et al. (Nucleic Acids Res., 2000, 28:e83). This technique involves using a puromycin linker with a 5' terminal psoralen moiety. UV irradiation is used to crosslink the peptide acceptor to the 3' end of the RNA.

Figure 1:
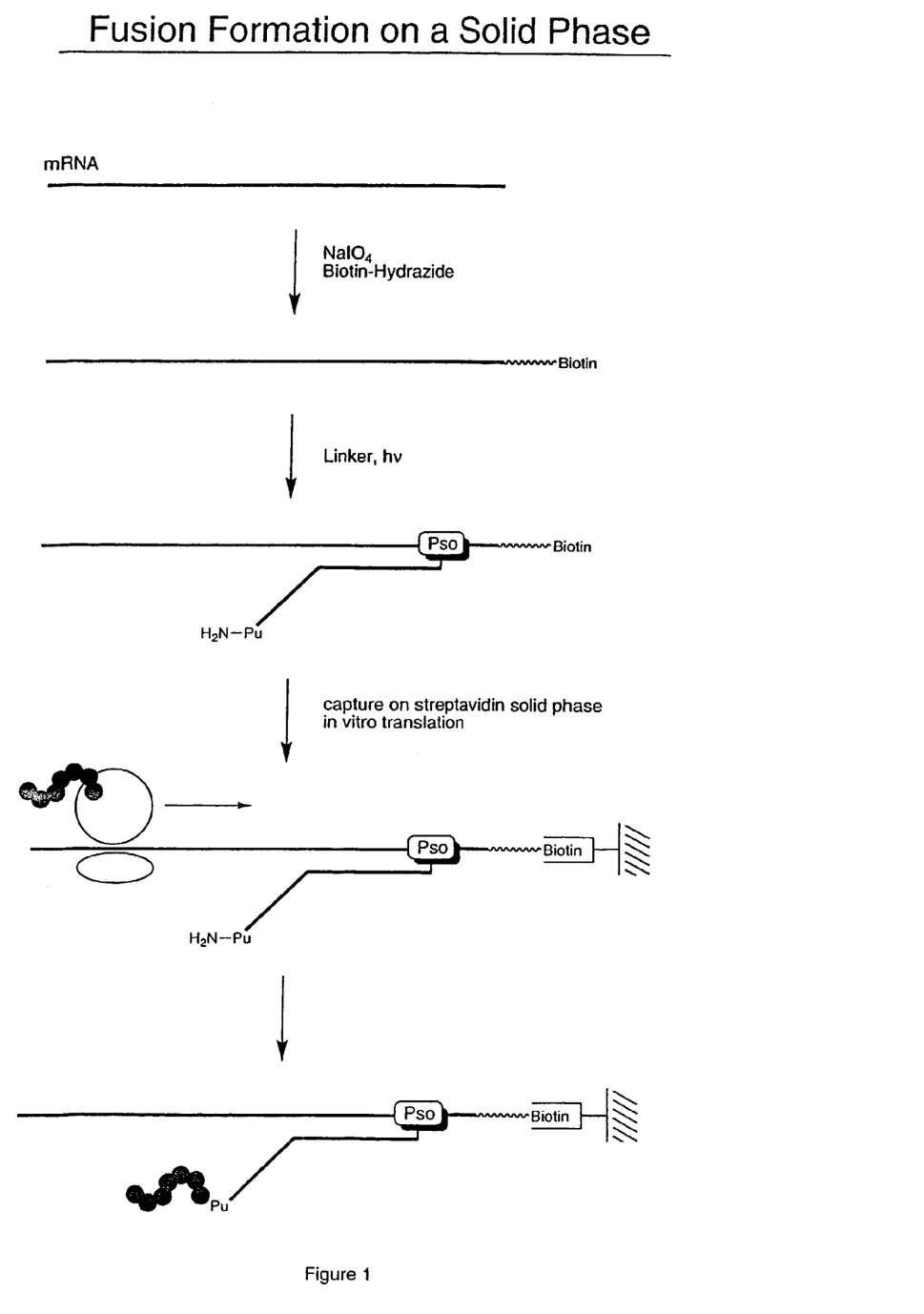
FIG. 1 is a schematic diagram showing a method of preparing protein-RNA fusions on a solid support. The RNA portion is proximal to the support and the protein is exposed for interaction with other compounds.

The present invention provides novel methods for immobilizing a template onto a solid support. In a first embodiment, outlined in FIG. 1, the template is attached to the support through its RNA. Prior to attachment, the RNA is modified to have a functional group, or an affinity molecule, at the 3' end. Any of the known functional groups (e.g., thiol or amino), or affinity molecules (e.g., biotin) are appropriate and methods for adding such groups are well-known. (See, e.g., Agrawal, Methods in Molecular Biological, Agrawal, ed., vol. 26, Totowa: Humana Press, 1994, pages 93–120). Functionalization of the 3' end can be performed before or after the RNA is linked to the peptide acceptor, and may be achieved using commercially available reagents. The functional group or affinity molecule allows for the RNA to be immobilized on the capture surface (e.g., a streptavidin surface is used to capture templates containing biotin; (See FIG. 1). The RNA may be immobilized prior to linking it to the peptide acceptor, or, as shown in FIG. 1, immobilization may occur after the RNA has been joined to the peptide acceptor.

Figure 2:
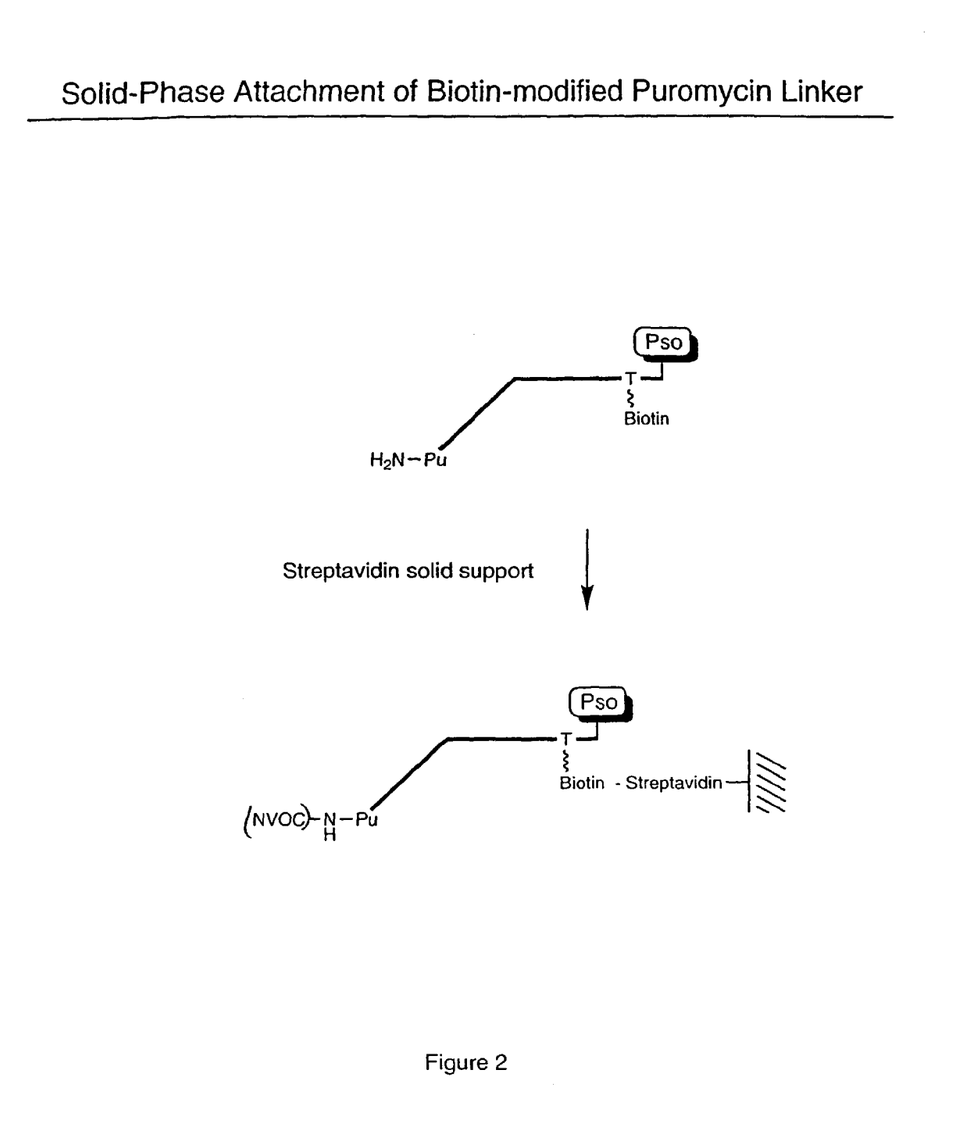
FIG. 2 is a schematic diagram showing solid-phase attachment of a biotin-modified puromycin linker on a streptavidin-coated support.
Figure 3:
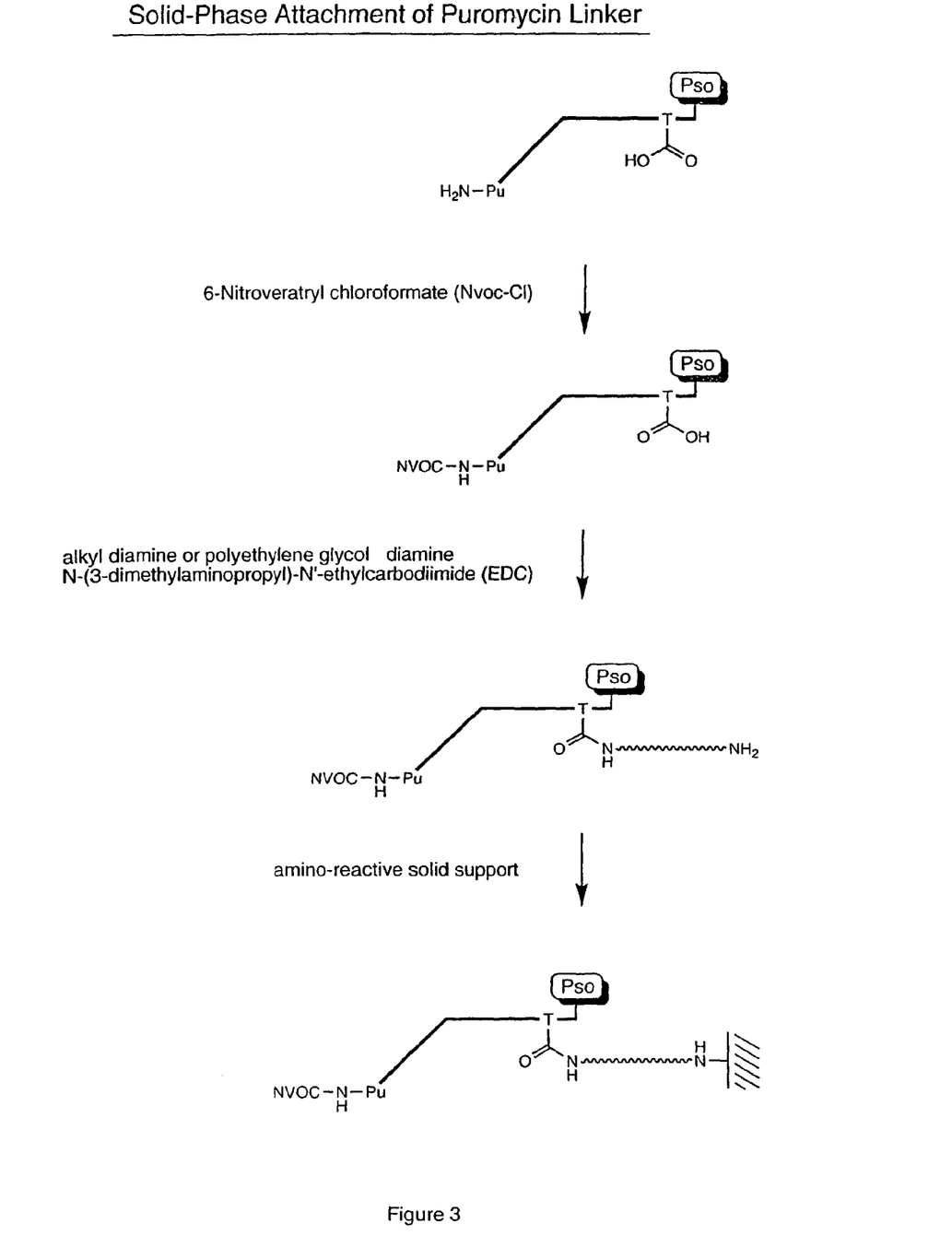
FIG. 3 is a schematic diagram showing steps for modification of a puromycin linker, with amino-functionalized spacer and capture on an amino-reactive support.

In a second embodiment the template is attached to the solid support through its linker portion (see FIGS. 2 and 3). The peptide acceptor-linker is first modified to allow its attachment to a solid support. The linker can be modified to include a suitable functional group (e.g., amine, or thiol), or an affinity molecule, such as biotin, that allows for capture on an appropriate surface. In a preferred embodiment, the linker is modified to include a side chain bearing the functional group. Preferred examples of suitable side chains include, without limitation, flexible and long alkyl- or polyethylene glycol chains.

Figure 4:
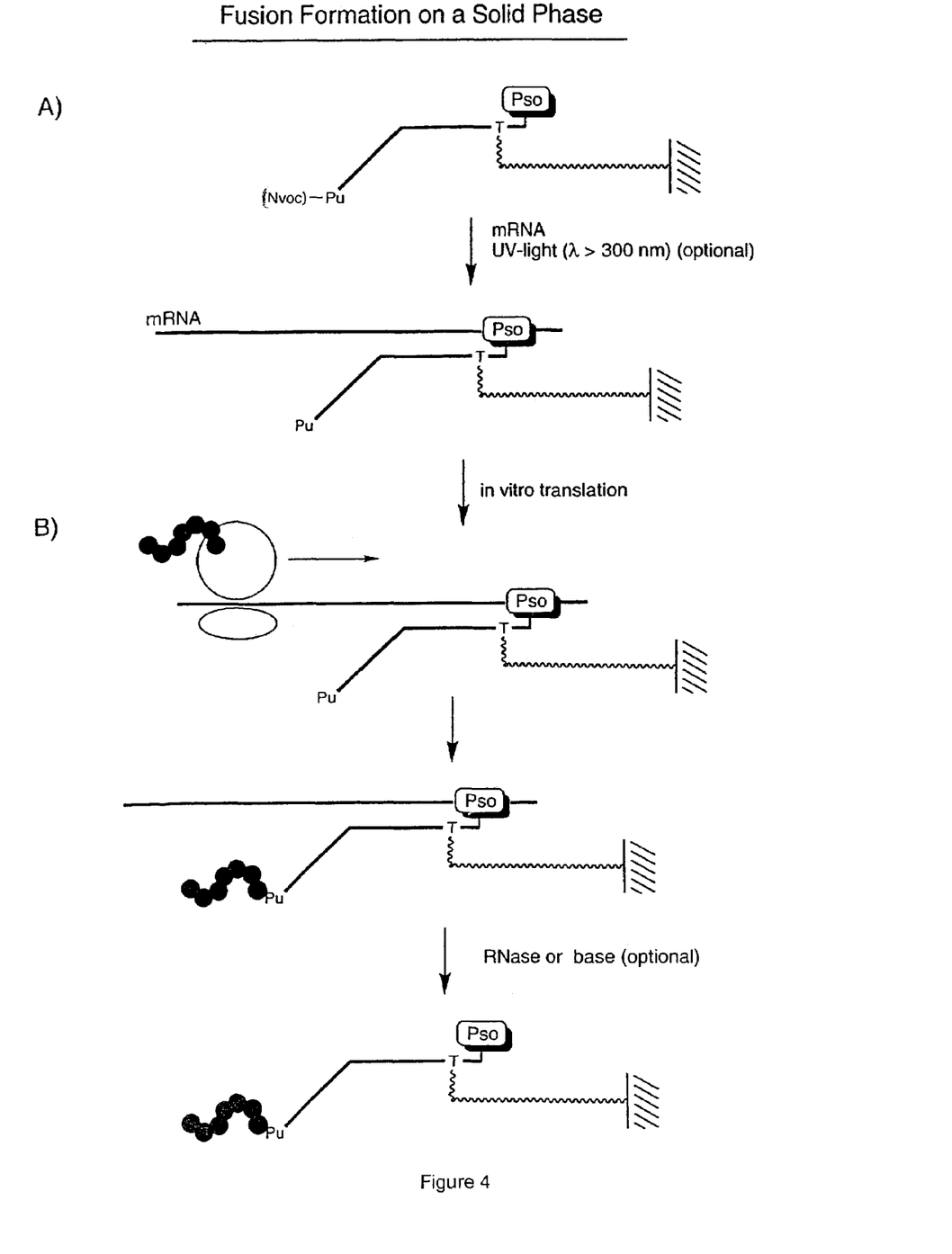

The linker is generally functionalized before being linked to the RNA. The linker is immobilized followed by ligation to the RNA, as shown in FIG. 4. Alternatively, the RNA may be joined to the peptide acceptor prior to attachment to the solid support.

A variety of materials may be used as the solid support. Examples of suitable support materials include, but are not limited to, natural polymeric materials, particularly cellulosic materials and materials derived from cellulose, such as fiber-containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methyl-butene), polystyrene, polymethacrylate, poly(ethylene terephthalate), nylon, poly(vinyl butyrate), etc.; either used by themselves or in conjunction with other materials; inorganic materials such as silica, magnesium sulfate, and alumina; or glass, silcon-glass, ceramics, metals (e.g., gold), and the like. These materials may be in the form of membranes, filters, chips, slides, wafers, fibers, magnetic or non-magnetic beads, gels, capillaries or other tubing, plates, polymers, and microparticles and can have a variety of surface features including wells, trenches, pins, and pores. Beads and microchips, particularly glass microchips, represent a preferred solid support surface.

Immobilization of an mRNA-puromycin Template Through the RNA Portion of the Template.

As discussed above, modification of the RNA to allow for its attachment to a solid phase can be performed either before or after ligation to a peptide acceptor-linker. Modification methods are known in the art, for example, periodate oxidation of the 3-terminal ribose (Agrawal, Methods in Molecular Biology, Agrawal ed., vol. 26, Totowa:Humana Press, pp. 93–120 (1994)), followed by reaction with an aldehyde-reactive reagent. The modification can be with biotin hydrazide (Pierce, Rockford, Ill.), or reductive amination with biotin amine conjugates (Pierce, Rockford, Ill.) or a diamine reagent (preferably a long-chain alkyl or polyethylene glycol diamine (Shearwater Polymers, Huntsville, Ala.) for capture on streptavidin-modified surfaces (e.g., streptavidin beads or glass-slides) or amino-capture surfaces (e.g., Xenobind microscopic slides (Xenophore, Hawthorne, N.J.)), respectively. Any method (e.g., chemical, enzymatic) for selective modification of an RNA 3'-region can be used (e.g., Kurz et al., U.S. Pat. No. 6,429,300 B 1).

Immobilization of an mRNA-puromycin Template Through the Puromycin-linker Portion of the Template The peptide acceptor-linker may also be modified to allow for its attachment to a solid phase. First, a side chain (preferably a flexible and long alkyl- or polyethylene glycol chain) that bears a suitable functional group (e.g., amine, thiol) or affinity molecule (e.g., biotin) is attached to the linker. This attachment can be done during the chemical synthesis of the linker by using appropriate phosphoramidite reagents (e.g., biotin-dT phosphoramidite (Glen Research, Sterling, Va.)) as shown in FIG. 2. Alternatively, attachment of a side chain can be accomplished, as shown in FIG. 3, through post-synthesis modification, following the incorporation of carboxy-dT phosphoramidite (Glen Research, Sterling, Va.) into the linker, such as contact with an amino functionalized spacer using standard peptide chemistry.

When the solid phase attachment is accomplished through amino capture, the puromycin amine should be masked (see FIG. 3). When using a photocrosslinking psoralen-puromycin linker conjugate (as described in Kurz et al. Nucleic Acids Res., 2000, 28:e83) the puromycin amine is preferably protected with a light-cleavable protecting group (e.g., nitroveratryloxycarbonyl (NVOC) (Pillai, Synthesis, 1980, 1).

mRNA encoding a peptide of interest can be ligated to a psoralen-puromycin linker and the resulting mRNA-puromycin template attached to a solid surface. Alternatively, the photocrosslinking psoralen-puromycin linker can be immobilized on the solid surface and mRNA added, for example, by incubating the entire surface with a solution of mRNA or by spotting mRNA solution into spatially defined features on the surface. Upon irradiation with UV light, the mRNA is crosslinked to the linker thereby being immobilized on the surface (FIGS. 4A and B). This immobilization of mRNA template to the surface is also applicable to preparations of mRNA that are hybridized to the puromycin linker without cross-linking such as described in Kurz et al., WO 01/07657.

Translation and Fusion Formation

By immobilizing an mRNA-puromycin template onto a solid support, the present invention provides a means for synthesizing the protein coded by the mRNA directly on the support. Once the template has been immobilized, a translation reaction is performed in order to generate the protein. Any translation system which allows for formation of an RNA-protein fusion and which does not significantly degrade the RNA portion of the fusion is useful in the invention. The translation reaction can be carried out, for example, as described in U.S. Pat. Nos. 6,258,558 B1, 6,261,804 B1; WO 98/31700; WO 00/47775; Roberts & Szostak, Proc. Natl. Acad. Sci. USA 1997, 94:12297; Roberts, Curr. Opin. Chem. Biol. 1999, 3:268; and Liu et al., Methods Enzymol. 2000, 318:268, which describe the generation of protein fusions using mRNA-puromycin templates. During translation, a ribosome moves along the mRNA to generate a nascent protein. The ribosome reaches the end of the open reading frame and pauses when it encounters the linker, allowing for the acceptor moiety to occupy the A site and accept the nascent peptide chain to generate an RNA-protein fusion. In the present invention, the peptide acceptor has been attached to a solid support and thus, formation of a covalent link between the C-terminus of the protein and the peptide acceptor results in immobilization of the protein.

In the embodiment that involves attaching the template to the solid support via its linker portion, it is envisioned that the RNA molecule can be removed after translation, leaving just the linker-protein portion on the solid phase (FIG. 4B). This is accomplished using any suitable technique, including, without limitation, nuclease or hydroxide treatment.

The protein immobilization techniques described herein are useful for applications in parallel screening of protein-protein and protein-compound interactions, for example, for drug discovery, and for the synthesis of protein microarrays for screening and diagnostic purposes.

Figure 5:
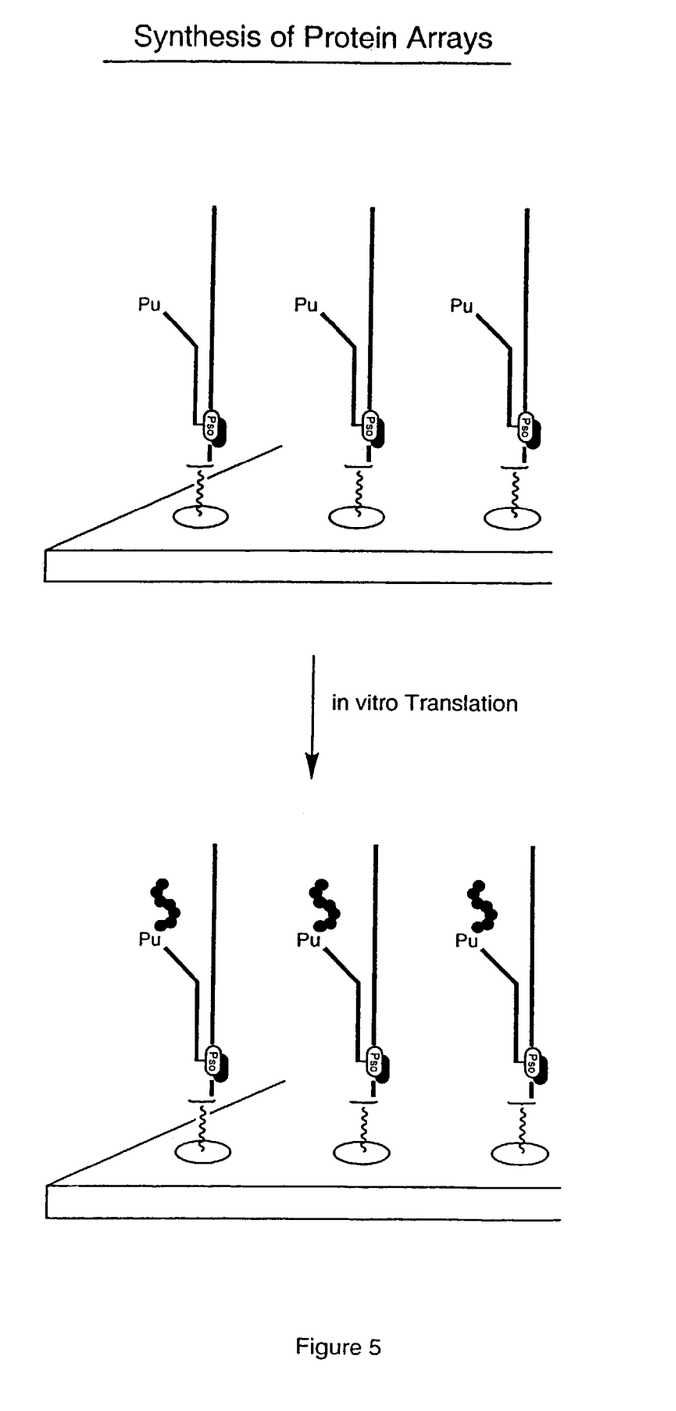
FIG. 5 is a schematic diagram showing synthesis of a protein array by in vitro translation of immobilized mRNA-puromycin-linker templates to form immobilized protein-RNA fusions

FIG. 5 illustrates the synthesis of a protein array using the immobilization methods of the invention. In this embodiment, various templates are immobilized in an array on a solid support. A single in vitro translation reaction is then performed to create an array of proteins immobilized on the support. A multi-feature array can be created through spotting individual templates onto a surface, followed by one common in vitro translation. Such arrays are particularly useful for parallel screening of compounds that may interact with the immobilized proteins.

In an alternative embodiment a spatially defined array can be generated on beads. The method of the invention can be used to immobilize templates onto beads so that each bead contains a template for just one protein type. The translation step to produce RNA-protein fusions can be performed in a single reaction containing all the beads. The use of labeled beads and a cell sorter for screening the beads, allows for separating the beads according to the proteins immobilized on their surfaces.

The present invention is illustrated by the following examples, which are in no way intended to be limiting of the invention.

EXAMPLE 1

Periodate Oxidation, Biotinylation of RNA

For this illustrative example, the RNA encodes a peptide having the amino acid sequence: MVSDVPRDLEVVAATPTSLLISWK-THEVAARYYRITYGETGGNSPVQEFTVPPW ASI-ATISGLKPGVDYTITVYAVTPLRW-TETEAHIPIPINYRT (SEQ. ID NO: 1) The RNA was modified to allow attachment to a solid phase. Modification of the RNA was performed by periodate oxidation of the 3'-terminal ribose (Agrawal Methods in Molecular Biology, Agrawal ed. Vol. 26, Totowa: Human Press, pp. 93–120 (1994)). This was accomplished by mixing 18 µL of RNA (10 µM), 10 µL of NaIO$_4$ (0.5 M), and 3.3 µL of NaOAc (0.1 M) in 68.7 µL of water and incubating for 15 minutes at room temperature.

Following incubation, the sample was precipitated with a solution of 260 µL H$_2$O, 40 µL NaOAc (3 M), and 1 mL EtOH, and re-suspended in 90 µL NaOAc (0.1 M). 10 µL of Biotin-LC-hydrazide, 50 mM (Pierce, Rockford, Ill.) was added. The mixture was incubated for 2 hours at room temperature and precipitated with NaOAc/EtOH as described above. The precipitate was re-suspended in 88.5 µL H$_2$O to which 1.5 µL PEG-6 linker (1 mM) and 10 µL 10×photobuffer (1 M NaCl, 250 mM Tris-HCl, pH 7) were added. The composition of the PEG-6 linker was 5' Pso u agc gga ugc XXX XXX CC Pu (Pso=C6-Psoralen u, a, g, c=2-MeO-RNA; A,C=standard amidites; X=Spacer 9; Pu=Puromycin-CPG)(SEQ. ID NO: 2). The reaction mixture was irradiated for 15 minutes at room temperature in a borosilicate glass vial.

EXAMPLE 2

On-Bead Fusion Formation

Biotinylated RNA was immobilized on a solid support by mixing 3 µL Bio RNA (and non-biotinylated control), 50 µL buffer (25 mM Tris, pH 7.0; 0.25% Tween), and 25 µL Neutravidin agarose beads. The mixture was incubated at room temperature for 10 minutes and spun in a Microspin column, followed by washing (2×) with 100 µL of buffer (1% BSA in PBS; 0.25% Tween) and washing (2×) with 100 µL of PBS/0.25% Tween buffer. A translation reaction was performed (see, e.g., Roberts & Szostak, Proc. Natl. Acad. Sci. USA, 1997, 94:12297 or Liu et al., Methods Enzymol., 2000, 318:268) by adding 100 µL lysate mix containing [$^{35}$S] Methionine. The mixture was rotated for 1 hour at 30° C. The mixture was then spun and 200 µL of 0.5 M KCl and 0.1 M MgCl$_2$ were added to promote RNA-protein fusion formation. The mixture was incubated for 1 hour at room temperature, spun, and washed (5×) with 100 µL PBS buffer. The sample was re-suspended in 100 µL of buffer and the successful formation of RNA-protein fusion formation was confirmed by scintillation counting of incorporated [$^{35}$S] Methionine.

EXAMPLE 3

On-Membrane Fusion Formation

Biotinylated RNA was diluted 1:5, 1:10, 1:20, 1:40, and 1:80 into 25 mM buffer (Tris, pH 7.0; 0.25% Tween-20). 3 µL aliquots were spotted on a dry streptavidin membrane (SAM™ Biotin Capture membrane, Promega, Madison, Wis.). The filter was then washed with buffer (1% BSA in PBS, pH 7.6; 0.25% Tween) and left to dry. A translation reaction was performed by soaking the filter with lysate ([$^{35}$S] Methionine) and incubating for 1 hour at 30° C. 0.5 M KCl and 0.1 mM MgCl$_2$ were added and the mixture was incubated for 1 hour at room temperature. The filter was then washed for 10 minutes with PBS buffer, rinsed thoroughly, dried, and exposed to a phosphorimager screen for analysis.

Other Embodiments

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications, patents, and patent applications mentioned in this specification are herein incorporated by reference.

What is claimed is:

1. A solid support having at least one RNA-protein fusion component immobilized thereon, wherein said RNA-protein fusion component comprises a protein covalently bonded at its C-terminus to a peptide acceptor, wherein said peptide acceptor is joined through a linker to the RNA which encodes the protein, wherein the linker comprises a non-nucleotide moiety, said RNA-protein fusion component being attached to the solid support by the interaction of said linker and said solid support.

2. The solid support of claim 1, wherein said linker comprises a biotin component and the solid support comprises a steptavidin component and said RNA-protein fusion component is attached to said solid support via binding of said biotin component to said streptavidin component.

3. The solid support of claim 1, wherein said linker comprises a sequence that is complementary to a portion of said RNA and is hybridized to said portion of said RNA.

4. The solid support of claim 3, wherein said sequence is a PNA sequence.

5. The solid support of claim 3 wherein said linker further comprises a psoralen moiety that is cross-linked to said RNA.

6. The solid support of claim 1, wherein said support comprises a plurality of immobilized proteins that form an array.

7. A method for screening for a molecule in a population of molecules for its ability to interact with a protein, said method comprising the steps of:
   (a) providing the solid support of claim 1;
   (b) contacting a population of molecules with said solid support; and
   (c) detecting the interaction of a molecule in said population with an immobilized protein of said solid support, thereby screening for a molecule in a population of molecules for its ability to interact with a protein.

8. A method for screening for a protein in a plurality of proteins for its ability to interact with a component of a sample, said method comprising the steps of:
   (a) providing the solid support of claim 1;
   (b) contacting said sample with said solid support; and
   (c) detecting an interaction of a component of said sample with an immobilized protein of said solid support, thereby screening for a protein in a plurality of proteins for its ability to interact with a component of a sample.

* * * * *